United States Patent [19]

Wex

[11] Patent Number: 5,190,524
[45] Date of Patent: Mar. 2, 1993

[54] DEVICE FOR BRINGING TOGETHER SEVERAL INFUSIONS AND/OR INJECTIONS

[76] Inventor: Roland Wex, Am Hang 28, D-3508, Meisungen, Fed. Rep. of Germany

[21] Appl. No.: 652,937

[22] Filed: Feb. 8, 1991

[30] Foreign Application Priority Data

Feb. 10, 1990 [DE] Fed. Rep. of Germany ....... 4004134

[51] Int. Cl.$^5$ ...................... A61M 5/14; A61M 37/00
[52] U.S. Cl. ...................................... 604/80; 604/83; 604/247
[58] Field of Search ................................ 604/80–89, 604/56, 246–248, 256, 258, 126; 128/DIG. 12

[56] References Cited

U.S. PATENT DOCUMENTS

| | | | |
|---|---|---|---|
| 3,416,567 | 12/1968 | Von Dardel et al. | 604/83 X |
| 4,447,230 | 5/1984 | Gula et al. | 604/122 |
| 4,604,093 | 8/1986 | Brown et al. | 604/248 |
| 4,666,429 | 5/1987 | Stone | 604/83 |
| 4,696,671 | 9/1987 | Epstein et al. | 604/67 |
| 4,769,017 | 9/1988 | Fath et al. | 604/283 |
| 4,828,587 | 5/1989 | Baurmeister et al. | 55/159 |
| 4,908,018 | 5/1990 | Thomsen | 604/83 |
| 4,915,688 | 4/1990 | Bischof et al. | 604/83 |

FOREIGN PATENT DOCUMENTS

| | | | |
|---|---|---|---|
| 0737249 | 6/1966 | Canada | 604/83 |
| 1216489 | 5/1966 | Fed. Rep. of Germany. | |
| 1907296 | 9/1969 | Fed. Rep. of Germany | 604/258 |
| 3520044A1 | 12/1986 | Fed. Rep. of Germany. | |

WO88/03815  6/1988  World Int. Prop. O. .

Primary Examiner—John D. Yasko
Assistant Examiner—Adam J. Cermak
Attorney, Agent, or Firm—Robert P. Simpson; Michael L. Dunn; Arthur S. Cookfair

[57] ABSTRACT

In a device for combining a plurality of liquid infusions to form a mixture comprising a chamber having a circumference and a plurality of separately closable inlets for various infusion liquids and an outlet for the mixture, and improvement is provided which comprises a chamber having a first chamber portion having inlets, a second chamber portion and an elastic sealing element held in an outer region of the circumference and interposed between the first and second portions, the sealing element extending over and covering the inlets, and segments of the sealing element being prestressed against such inlets to close same, each of the inlets communicating with the chamber and the outlet when the elastic sealing element is removed from covering each such inlet, wherein the separately closable inlets are disposed radially about an axis and the outlet is disposed longitudinally along the axis, wherein the inlets are located proximate the circumference of the chamber and each inlet ends in a sealing element opening space connected with the outlet, and wherein the sealing element has an inner circumference, and is disposed concentrically with the outlet, wherein the inner circumference terminates at a distance from an inner boundary of the opening space.

18 Claims, 1 Drawing Sheet

DEVICE FOR BRINGING TOGETHER SEVERAL INFUSIONS AND/OR INJECTIONS

BACKGROUND OF THE INVENTION

The invention relates to a device for bringing together several infusions and/or injections, said device consisting of a chamber through which flows the infusion/injection liquid and which is provided with several radially disposed, separately closable inlets and one outlet for the blended liquid.

Such a device is known from W. German Patent [DE] 35 20 044 A1. It can be used to administer and/or prepare drug and/or nutrient solutions, particularly parenteral nutrient solutions, and to administer injections. For each inlet, there is one check valve which can only be opened in the direction of the outlet toward the patient, said valve, in particular, having the form of a spout.

The advantage of the known device over the known stopcock arrangements wherein mechanically actuated rotary stopcocks are provided for the inlets is that the inlets do not have to be actuated manually. Said device has the drawback, however, that the fabrication of the individual check valves is quite expensive and that the construction of the device is complicated.

SUMMARY OF THE INVENTION

It is the object of the present invention to provide a device of the said kind which is based on simple constructive means and simple construction and ensures reliable, manipulation-free closure of the individual inlets. In addition, the device is suitable for gravity flow as well as for pumped infusions.

This objective is reached by means of a chamber consisting of a first part which is fitted with the inlets and a second part, between which parts an elastic sealing element extends at least over the angle formed by the inlets, said chamber being held in the external region of its circumference, each inlet ending in a sealing element opening space that is linked with the outlet, and the sealing element segment corresponding to the opening space being prestressed against the inlet.

Hence, an essential feature of the present invention is the sealing element whose function it is not only to seal the two parts of the chamber against each other, but also to act as a valve. Where there are no opening spaces, the single sealing element is fastened between the two parts of the chamber and, hence, yields against the prestressing force, in the direction away from the inlets, only in the region of the opening spaces. The sealing element segments may be prestressed as desired, for example by subjecting the sealing element to a deformation in the area of the sealing element segments thus imparting to it an inherent tension, or by providing an elastic element between a sealing element segment and the part of the chamber that is turned away from the inlet, said elastic element being compressed during the introduction of a liquid, namely an infusion or an injection, by the sealing element segment that is raised away from the opening. The sealing element consists, for example, of silicone, rubber or an elastomer. It may be provided with slits disposed on both sides of a particular inlet and oriented in the flow direction, said slits forming between themselves a sealing flap so as to facilitate the opening movement of the sealing element segment when said segment is subjected to a reduced prestress.

The sealing of the inlets by means of identically acting sealing element segments ensures that for identical inflow conditions all inlets will have the same transport capacity. Moreover, because of the prestressed sealing element segments, all feed streams are protected against backflow. In this respect, the radial disposition of the inflowing streams assumes special importance in that it not only permits several infusions and/or injections to be brought together in a very small space and ensures an ergonomically favorable arrangement of the inflowing streams, but it also represents a particularly simple constructive design of the chamber and of the sealing element. In a preferred embodiment of the invention, the sealing element is concentric with the outlet and ends with its inner circumference at a distance from the opening space. The advantage of this arrangement lies in that the liquid flows from the inlets radially inward on a direct path toward the outlet, the flow being guided in optimum manner because of the short flow paths while at the same time the liquids are intensively mixed.

It is particularly advantageous for the first part of the chamber to have in the area of each inlet a convexity bulging away from the second part of the chamber, said convexity being associated with an inlet opening, and for the corresponding sealing element segment in the area of said convexity to have an essentially corresponding convexity. Thus, the sealing of the individual inlet openings occurs in the area of the corresponding convexities by co-operation of the convex areas of the sealing element segments with the convex areas of the first part of the chamber. During the introduction of the liquid, the stressed arrangement of the sealing element in the immediate vicinity of its convex regions causes the top of the convex sealing element segment to be raised away from the inlet opening segment and, at the end of liquid introduction, to resume immediately its uniformly convex position in which the inlet opening is closed. It is advantageous for the second part of the chamber to have in the area of each inlet a convexity directed toward the first part of the chamber and which, when the flow of liquid is shut off, leaves a free gap on the side of the corresponding sealing element segment. In this manner, when the inlet is opened, said convex sealing element segment can be raised away from the first part of the chamber, but only until it touches the second part of the chamber. Excessive movement of the sealing element segment is thus prevented. The described embodiment also has the advantage that the sealing element can be installed in only one way. Advantageously, the parts of the chamber and the sealing element segments have the shape of a semishell. To ensure unambiguous prestressing of the sealing element segments, said segments should, in the unstressed, namely unmounted, state, present a convexity that is smaller than that of the first part of the chamber. When the two parts of the chamber are assembled, a slightly lesser curvature of the sealing element segments is sufficient to enable the entire convexity of said segments to be pressed into the corresponding convexity of the first part of the chamber.

In a special arrangement of the sealing element, the outer circumference of said element is provided with an axial attachment, and the sealing element is fastened between the outer radial areas of the chamber parts and between the axial areas corresponding to the axial attachment. Advantageously, the chamber is essentially flat, and the sealing element opening spaces end radially in a flat liquid-collecting space limited by the two parts of the chamber, to which space is connected the centrally and preferably axially disposed outlet that leads to the patient. When the chamber is of flat design, the sealing element segments, which suitably are internally radially separated, end at an overflow partition which is disposed between an opening space and the liquid-collecting space. The overflow partition ensures that when liquid is being introduced through the other inlets of the device, the liquid cannot flow under the sealing element segment of that inlet through which no liquid is flowing and, moreover, that pressure will build up on the lip-like sealing element segment.

To prevent microparticles from passing through the outlet on the patient side, it is advantageous to insert a hydrophilic membrane into the flow path of the liquid between the sealing element opening spaces and the outlet in the liquid-collecting space. Moreover, for the purpose of forced deaeration of the effluent on the patient side, the chamber is provided with deaeration orifices associated with a hydrophobic membrane. Advantageously, the first part of the chamber constitutes the lower, and the second part the upper, part of the chamber in which case the deaeration orifices are on the upper part of the chamber. Preferably, the sealing element is concentric with the hydrophilic and/or hydrophobic membrane.

To simplify the use of the device as much as possible and to be able to hold said device in position for long periods of time, which is especially important for infusions, the chamber consists of a semicircular segment, with radial inlets disposed over the semicircular sector and a holding plate oriented in the plane of the semicircular segment. By means of the holding plate, it is possible, for example, to fasten the device onto a stand making sure that the inlets are disposed horizontally and the outlet is directed vertically downward. This will greatly simplify handling and reduce the risk of pinching the tubing carrying the inflowing liquids.

Finally, it is also possible to protect the inlets and the outlet from contamination and air by use of a cap (Luer lock), and the infusion lines can be provided with separate clamps for the purpose of fully clamping off the infusion lines or of metering the flow in said infusion lines. Moreover, several devices can be connected in parallel or in series. To differentiate the individal inlets, said inlets are suitably color-coded.

Other features of the invention will become apparent from the decription of the figures and from the subordinate claims. In this respect, it should be noted that all individual features and all combinations of individual features constitute additional embodiments of the invention.

BRIEF DESCRIPTION OF THE DRAWING

In the figures, the invention is exemplified by way of a particular embodiment without being limited to it. In the drawings.

DESCRIPTION OF THE PREFERRED EMBODIMENT

Figure 1:
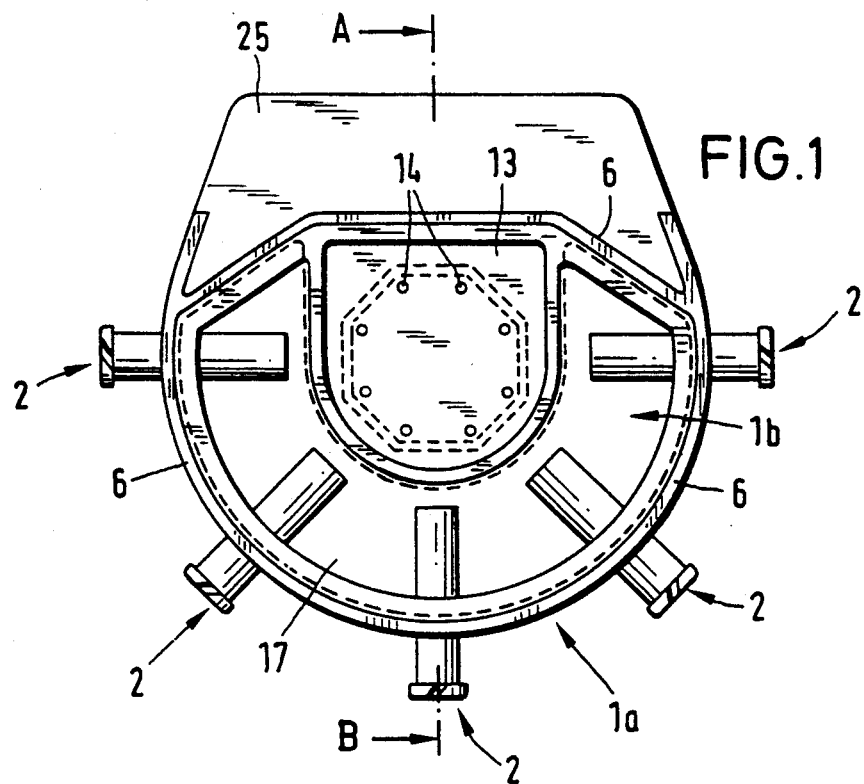
FIG. 1 is a top view of the device of the invention (view X according to FIG. 2)

The device shown in the drawings represents a collector for infusions and/or injections which is suitable for both gravity and pumped infusions. It consists of a chamber 1 with five inlets 2 which are offset at a 45° angle and which in use position of the device to be described in the following are disposed horizontally, and of downward oriented outlet 3.

In detail, chamber 1 consists of an essentially flat, horizontally oriented lower chamber part 1a and a flat upper chamber part 1b. The lower chamber part 1a has a central segment 4 extending essentially over a semicircle and to which is attached in downward orientation, as outlet 3, a connection piece 5 with a Luer lock fitting. Laterally, central segment 4 is limited by wraparound edge 6 which is vertical relative to said segment and extends away from the connection piece. In the area of inlets 2, the lower chamber part 1a is bent downward at a right angle. Each inlet 2 has a connection piece 7 with a Luer lock fitting and an angular channel with a radial channel segment 8 starting at connection piece 7 and an adjoining, axially upward oriented channel segment 9. Radially within the outlet opening of channel segment 9, lower chamber part 1a is provided with a slightly upward extending crosspiece 10 which is disposed over a semicircle in conformity with the arrangement of inlets 2 and in the area of its two ends is prolonged by a straight segment. As can be seen, in particular, from the drawing of FIG. 3, radially outside crosspiece 10 the lower chamber part 1a is shaped as a downward bulging semishell 15 which when viewed radially outward is inclined downward.

Figure 2:
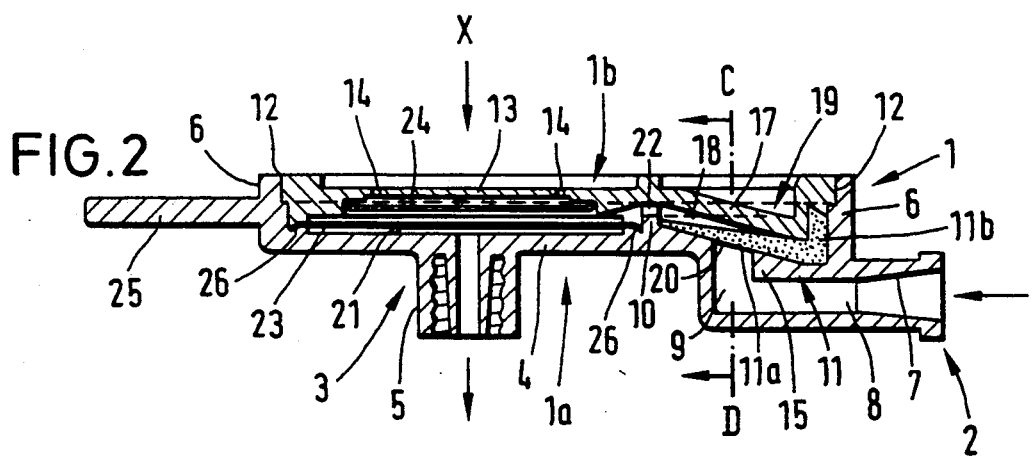
FIG. 2 is a section across the device along line A–B in FIG. 1.
Figure 3:
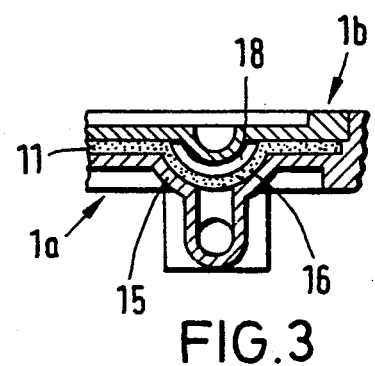
FIG. 3 is a section through the device in the area of an inlet along line C–D in FIG. 2.

Inserted between wraparound edge 6 and crosspiece 10 is an elastic sealing element 11 consisting, for example, of silicone. As shown in FIG. 1 by a broken line, this element extends, in conformity with the arrangement of inlets 2, over a semicircle and ends internally at a slight distance from crosspiece 10. At its end that faces crosspiece 10, the sealing element is relatively narrow and in the form of a sealing lip. Sealing segment 11a of the sealing element associated with the sealing lip broadens outward and continues vertically thereto in the form of a storage segment 11b. In the area of inlets 2, as shown in FIGS. 2 and 3, sealing segment 11a is shaped to conform to semishell 15 of lower chamber part 1a so that here semishell 16 of sealing element 11 rests against semishell 15 of lower chamber part 1a. In detail, the curvature of semishell 16 is slightly less than that of semishell 15.

Upper chamber part 1b is made so as to conform to the shape of wraparound edge 6 of lower chamber part 1a, namely it is essentially of semicircular shape, and is followed by a trapezoidal attachment. It can be fitted into lower chamber part 1a so that outer edge 12 of upper chamber part 1b cooperates in sealing manner with the inner contour of wraparound edge 6. Parallel to and at a distance from central segment 4 of lower chamber part 1a, upper chamber part 1b is provided with a central segment 13 which contains deaeration orifices 14. Connected to central segment 13 is an edge segment 19 which in the area of inlets 2, as shown in particular in FIG. 3, is also shaped as a semishell 17. The contours of semishells 15 and 17 that face each other run parallel to each other and form between themselves a sealing element opening space 18. When the chamber is assembled, the knee [elbow] of edge segment 19 formed in the area of inlets 2, in particular, presses the knee between sealing segment 11a and storage segment 11b of sealing element 11 against semishell 15 and, in general, sealing element 11 between neighboring inlets 2 is compressed between upper chamber part 1b and the lower part of the chamber. This, supported by the additional prestress that arises from the different convexities of semishell 16 of sealing element 11 and semishell 15 of lower chamber part 1a, causes reliable closing of opening 20 of inlets 2.

Between central segment 13 of upper chamber part 1b and central segment 4 of lower chamber part 1a is a liquid-collecting space 21 which through an overflow opening 22 located on the side of the crosspiece is in flow communication with each sealing element opening space 18 of corresponding inlet 2. In the lower part of the chamber, between overflow openings 22 and connection piece 5, is disposed a hydrophilic membrane 23, and on the other side, in upper chamber part 1b, is disposed, in front of deaeration orifices 14, a hydrophobic membrane 24. Sealing element 11 is disposed concentrically with membranes 23 and 24. Chamber 1 is configured symmetrically with respect to line A-, and lower chamber part 1a has a holding plate 25 on the side facing away from inlet 2 which is disposed in the symmetry plane.

The chamber consists, for example, of a moldable, transparent thermoplastic, particularly PVC [polyvinyl chloride]. Hydrophilic membrane 23 is, for example, welded to the raised ring segment 26 associated with central segment 4 of the lower part of the chamber, or said membrane is fastened between said ring segment and upper chamber part 1b. Similarly, hydrophobic membrane 24 is welded to a raised area of central segment 13 of upper chamber part 1b. After sealing element 11 is placed into the lower part of the chamber and upper chamber part 1b is fitted to lower chamber part 1a, the two parts of the chamber are advantageously also welded together. Advantageously, before the device of the invention is used, inlets 2 and outlet 3 are plugged by means of stoppers, and the inlets are color-coded.

Before the device is used, holding plate 25 is fastened to a stand with chamber 1 in horizontal position, outlet 3 is connected to the patient by means of tubing, and a number of infusion tubes which depends on the number of infusions are screwed onto inlets 2. During use, at sufficient pressure in the infusion line, the top area of sealing segment 11a of the corresponding sealing element 11 is moved away from opening 20 and from an area between opening 20 and the area of lower chamber part 1a that faces away from crosspiece 10. As a result, a small, oppositely directed bulging of semishell 16 takes place, and the liquid can flow radially inward through overflow opening 22 into liquid-collecting space 21 and from here to outlet 3. If the infusion line is pinched off, the change in pressure in the corresponding inlet 2 will immediately close the sealing element because of the prestress. Any liquid flow from other inlets 2 through which at the time no infusion or injection liquid is being admitted is excluded, because the liquid pressure acts on the side of sealing element 11 facing away from opening 20 thus causing an even higher closing pressure. The arrangement of crosspiece 10 with overflow opening 22 is advantageous, because according to the overflow principle it promotes a pressure rise in the area of the inner, lip-like end of the sealing element.

Figure 4:
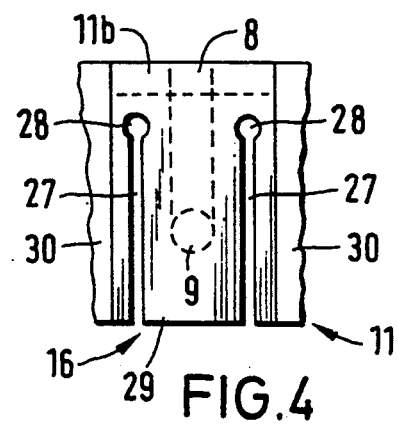
FIG. 4 is a bottom view of a modified version of a sealing element, in magnified representation.

FIG. 4 shows an embodiment that is modified compared to the aforedescribed design of sealing element 11. In this modification, semishell 16 of sealing element 11 which is disposed between the flat areas 30 of sealing element 11 is provided on both sides of channel segment 9 and at a distance therefrom with slits 27 disposed parallel to each other and parallel to radial channel segment 8, slit 27 being open in the vicinity of crosspiece 10 and the other end of the slit being fashioned as a hole 28. The resulting sealing flap 29 seals channel section 9 when the prestress is reduced.

| List of Reference Numerals | |
|---|---|
| 1 | Chamber |
| 1a | Lower chamber part |
| 1b | Upper chamber part |
| 2 | Inlet |
| 3 | Outlet |
| 4 | Central segment |
| 5 | Connecting piece |
| 6 | Wraparound edge |
| 7 | Connecting piece |
| 8 | Radial channel segment |
| 9 | Axial channel segment |
| 10 | Crosspiece |
| 11 | Sealing element |
| 11a | Sealing segment |
| 11b | Storage segment |
| 12 | Outer edge |
| 13 | Central segment |
| 14 | Deaeration orifice |
| 15 | Semishell |
| 16 | Semishell |
| 17 | Semishell |
| 18 | Sealing element opening space |
| 19 | Edge segment |
| 20 | Opening |
| 21 | Liquid-collecting space |
| 22 | Overflow opening |
| 23 | Hydrophilic membrane |
| 24 | Hydrophobic membrane |
| 25 | Holding plate |
| 26 | Ring segment |
| 27 | Slit |
| 28 | Hole |
| 29 | Sealing flap |
| 30 | Flat area |

What I claim is:

1. In a device for combining a plurality of liquid infusions to form a mixture comprising a chamber having a circumference and a plurality of separately closable inlets for various infusion liquids and an outlet for the mixture wherein the improvement comprises a chamber comprising a first chamber portion having inlets, a second chamber portion and an elastic sealing element held in an outer region of said circumference and interposed between the first and second portions, said sealing element extending over and covering the inlets, and segments of said sealing element being prestressed against such inlets to close same, each of said inlets communicating with the chamber and the outlet when the elastic sealing element is removed from covering each such inlet, wherein the separately closable inlets are disposed radially about an axis and said outlet is disposed longitudinally along said axis, wherein the inlets are located proximate the circumference of the chamber and each inlet ends in a sealing element opening space connected with the outlet, and wherein the sealing element has an inner circumference, and is disposed concentrically with the outlet, wherein the inner circumference terminates at a distance from an inner boundary of the opening space.

2. The device of claim 1 wherein the first chamber portion has a convexity, proximate each inlet, directed away from the second chamber portion, an opening of each inlet is disposed in each convexity and the sealing element segments are in the area of each convexity and are provided with an essentially corresponding convexity.

3. The device of claim 2 wherein the curvature of the convexity in the sealing element is smaller than the convexity in the first chamber when the prestress of the sealing element is reduced.

4. The device of claim 3 wherein an axial connecting piece is provided on the outer circumference of the sealing element and is fastened between outer radial areas of the chamber portions and axial areas of the chamber portions.

5. The device of claim 4 wherein the chamber is essentially flat and the sealing element opening spaces end radially in a flat liquid collecting space defined by the first and second chamber parts and the liquid collecting space is provided with a centrally located and axially disposed outlet.

6. The device according to claim 5 wherein the first chamber portion comprises a lower chamber portion and the second chamber portion comprises an upper chamber portion.

7. The device according to claim 6 wherein the upper chamber portion contains deaeration orifices in association with a hydrophobic membrane.

8. The device according to claim 4 wherein the first chamber portion comprises a lower chamber portion and the second chamber portion comprises an upper chamber portion.

9. The device according to claim 8 wherein the upper chamber portion contains deaeration orifices in association with a hydrophobic membrane.

10. The device according to claim 1 wherein the first chamber portion comprises a lower chamber portion and the second chamber portion comprises an upper chamber portion.

11. The device according to claim 10 wherein the upper chamber portion contains deaeration orifices in association with a hydrophobic membrane.

12. The device of claim 1 wherein the chamber is made of a semicircular segment lying in a plane substantially perpendicular to said axis with radial inlets disposed over the semicircular segment and of a holding plate which is connected to a base region of the semicircular segment, which holding plate is oriented in the plane of the segment.

13. The device of claim 1 wherein the sealing element is provided with slits disposed on both sides of each inlet and oriented in the flow direction, said slits forming a sealing flap between them.

14. In a device for combining a plurality of liquid infusions to form a mixture comprising a chamber having a circumference and a plurality of separately closable inlets for various infusion liquids and an outlet for the mixture wherein the improvement comprises a chamber comprising a first chamber portion having inlets, a second chamber portion and an elastic sealing element held in an outer region of said circumference and interposed between the first and second portions, said sealing element extending over and covering the inlets, and segments of said sealing element being prestressed against such inlets to close same, each of said inlets communicating with the chamber and the outlet when the elastic sealing element is removed from covering each such inlet, wherein the separately closable inlets are disposed radially about an axis and said outlet is disposed longitudinally along said axis, wherein the inlets are located proximate the circumference of the chamber and each inlet ends in a sealing element opening space connected with the outlet, and wherein the chamber is essentially flat and the sealing element opening spaces end radially in a flat liquid collecting space defined by the first and second chamber parts and the liquid collecting space is provided with a centrally located and axially disposed outlet.

15. The device of claim 14 wherein each sealing element segment ends internally and radially at a position removed from an overflow partition forming a part of the first chamber portion, said partition being disposed between the opening space and liquid collecting space.

16. The device of claim 14 wherein a hydrophilic membrane is disposed in the flow path of the liquid between the sealing element opening spaces and the outlet in the liquid collecting space.

17. The device according to claim 14 wherein the first chamber portion comprises a lower chamber portion and the second chamber portion comprises an upper chamber portion.

18. The device according to claim 17 wherein the upper chamber portion contains deaeration orifices in association with a hydrophobic membrane.

* * * * *